(12) United States Patent
Stewart et al.

(10) Patent No.: US 6,517,510 B1
(45) Date of Patent: Feb. 11, 2003

(54) AUTOMATIC PATIENT CONTROL DEVICE

(75) Inventors: Thomas P. Stewart, Orchard Park, NY (US); Hermann K. Pohl, Orchard Park, NY (US)

(73) Assignee: Gaymar Industries, Inc., Orchard Park, NY (US)

( * ) Notice: Subject to any disclaimer, the term of this patent is extended or adjusted under 35 U.S.C. 154(b) by 276 days.

(21) Appl. No.: 09/603,777

(22) Filed: Jun. 26, 2000

(51) Int. Cl.[7] ................................................ A61M 1/00
(52) U.S. Cl. ...................... 604/31; 604/6.11; 604/6.13; 604/23; 604/27; 604/30; 604/113; 604/114; 604/131; 604/151; 604/28; 604/500; 417/207
(58) Field of Search ................................ 604/113, 151, 604/6.11, 6.13, 23, 30, 114, 131, 27, 28, 500; 128/DIG. 13; 417/207

(56) References Cited

U.S. PATENT DOCUMENTS 4,691,762 A * 9/1987 Elkins et al. ................. 165/46
5,097,829 A * 3/1992 Quisenberry ................ 219/490
5,183,039 A * 2/1993 Sarian et al. ................. 165/46
6,149,674 A * 11/2000 Borders ....................... 607/96

FOREIGN PATENT DOCUMENTS

WO    WO 99/44552    9/1999

* cited by examiner

*Primary Examiner*—Thomas Denion
*Assistant Examiner*—Theresa Trieu
(74) *Attorney, Agent, or Firm*—Roach Brown McCarthy & Gruber, P.C.; Kevin D. McCarthy

(57) ABSTRACT

The present invention relates to regulating the temperature of a desired medium that is applied to the exterior surface of a mammal. These devices have been used in the past but not with the ability to control the temperature of the desired medium in a predetermined ratio to the temperature of the mammal. With such control, the present invention decreases the change of discomforting the patient when the patient's temperature is being brought to a set point temperature body temperature.

134 Claims, 10 Drawing Sheets

AUTOMATIC PATIENT CONTROL DEVICE

FIELD OF THE INVENTION

The present invention relates to an automatic patient control device that delivers a medium to a patient.

BACKGROUND OF THE INVENTION

Gaymar Industries, Inc. (the assignee of the present invention) is the owner and manufacturer of the MEDI-THERM II® hypo/hyperthermia machine. This machine delivers water to a blanket (i.e., Gaymar's Hypo/hyperthermia blanket, Gaymar's THERMACARE® blanket or Gaymar's MEDI-TEMP® blanket), a mattress pad (i.e., Gaymar's Alternating Pressure Pad (model no. EFF302)), a chair pad, or a mattress unit (i.e., Gaymar's CLINIDYNE® mattress) (collectively the blankets, pads, and mattresses and obvious variations thereof are hereinafter "Objects"). In particular, the Objects surround a patient or applied to predetermined portions of the patient.

The object of the MEDI-THERM II® hypo/hyperthennia machine is to stabilize a patient who is experiencing hypothermia or hyperthermia or, in some instances, to actively cause hypothermia or hyperthermia as therapy. To understand the MEDI-THERM II® device, we will revert to FIG. 1 (prior art) which is a flow diagram of how the MEDI-THERM II® device distributes water to and from an Object. The liquid medium enters MEDI-THERM II® device through return inlet 52. From return inlet 52, the liquid medium traverses through a first conduit 30 to a first solenoid valve 32 for cold liquid medium or a second solenoid valve 34 for warm liquid medium.

From the first solenoid valve 32, the liquid medium goes through a second conduit 36 and a first cold inlet 37 to a cold reservoir 38. The cold reservoir 38 is a conventional cooling unit that cools the water, i.e., a refrigeration system's or air conditioner's evaporator. The evaporator in the reservoir maintains a large quality of water at a predetermined temperature—normally 4° C.—(hereinafter "Cold Water"). Water entering the reservoir is cooled by mixing with the Cold Water already in the reservoir (hereinafter "Reservoir Water".) If the cold reservoir 38 overflows, the Cold Water escapes from the device 10 through an overflow outlet 40. The Cold Water then flows through a cold outlet 41 of the cold reservoir 38 and a third conduit 42 to a manifold 44.

Similarly from the second solenoid 34, the water goes to a hot reservoir 46 through a fourth conduit 48 and a hot inlet port 49. The hot reservoir 46 is a conventional heating apparatus that heats the liquid medium (hereinafter "Warm Water"). The Warm Water flows through the warm outlet 56 to the manifold 44.

At the manifold 44 the Warm Water and the Cold Water converge. The selection of which return water path is active and its length of time active is controlled via solenoid valves 32 and 34 to attain a desired temperature (hereinafter "Mixed Water"). The Mixed Water is drawn through a sixth conduit 74 by a conventional pump 76, to supply outlet 14. A flow switch 78 on the sixth conduit 74 senses whether the Mixed Water reaches the supply outlet 14. Obviously, when the flow switch 78 is on, the Mixed Water reaches the supply outlet 14. And when the flow switch 78 is off, the Mixed Water fails to reach the supply outlet 14. A seventh conduit 80 connects with the first conduit 30 to provide quelling of temperature overshoot when no Object is connected.

When the Mixed Water reaches the supply outlet 14, the Mixed Water is released into the outlet conduit 18 into the Object 16. The Mixed Water traverses through the Object 16 to the return conduit 50 and into the return inlet 52.

The Mixed Water temperature is altered with the first solenoid valve 32 which controls the Warm Water and the second solenoid valve 34 which controls the Cold Water. The amount of water each valve 32, 34 allows into the manifold 44 depends on the temperature of the mammal 20 and the temperature of the Mixed Water in the Object.

The temperature of the mammal 20 is measured by a first conventional temperature sensing device (i.e. thermistors or thermocouples) 130 connected to a preselected portion of the mammal 20 and interconnected to a processing unit 90. The measurement from the first temperature sensing device 130 is transmitted to a processing unit 90.

The temperature of the Mixed Water in the Object is measured by a second conventional temperature measuring device 132 placed in the Object 16, in the supply conduit 18, the supply outlet 14, the sixth conduit 74, or manifold 44. The measurement from the second temperature measuring device 132 is transmitted to the processing unit 90.

The processing unit 90 compares the measurement from the first temperature sensing device 130 (hereinafter "First Measurement") to the Set Point Body temperature of the mammal 20 (hereinafter "Set Point Body Temperature"). The processing unit 90 determines whether First Measurement is above or below the Set Point Body Temperature.

Initially when the First Measurement is above the Set Point Body Temperature, the MEDI-THERM II® device, by design, applies the coldest water available (normally 4° C.) to the Object 16. FIG. 2 (prior art) illustrates this design feature in section 200 wherein the temperature of the First Measurement is represented as line 201, the Set Point Body Temperature is represented as line 202, and the Mixed Water is represented as line 203. Once the First Measurement 201 falls below the Set Point Body Temperature 203, the processing unit uses the solenoid valves 32, 34 to alter the temperature of the Mixed Water, not at a predetermined differential from the First Measurement, to eventually stabilize the patient to the Set Point Body Temperature. See section 204 of FIG. 2.

Likewise, when the First Measurement is below the Set Point Body Temperature, the MEDI-THERM II® device, by design, applies the warmest water available (normally 42° C.) to the Object 16. Once the First Measurement 201 falls above the Set Point Body Temperature 203, the processing unit uses the solenoid valves 32, 34 to alter the temperature of the Mixed Water, not at a predetermined differential from the First Measurement, to eventually stabilize the patient to the Set Point Body Temperature. See section 204 of FIG. 2.

The MEDI-THERM II® device, however, can sometimes cause discomfort to the patient. This discomfort can occur when the MEDI-THERM II® device applies the coldest water available (normally 4° C.) or the warmest water available (normally 42° C.) into the Object during the initial time frame, shown in section 200 of FIG. 2, or when the First Measurement and the Set Point Body Temperature difference is not-so-great but exists for a long time. When the patient is exposed to the coldest or warmest water available, the patient may experience some discomfort.

The present invention solves this problem.

SUMMARY OF THE PRESENT INVENTION

The present invention relates to regulating the temperature of a desired medium that is applied to the exterior surface of a mammal. These devices have been used in the past but not with the ability to control the temperature of the desired medium in a predetermined ratio to the temperature of the mammal. With such control, the present invention decreases the chance of discomforting the patient when the patient's temperature is being brought to a Set Point Body temperature.

DETAILED DESCRIPTION OF THE PRESENT INVENTION

Figure 1:
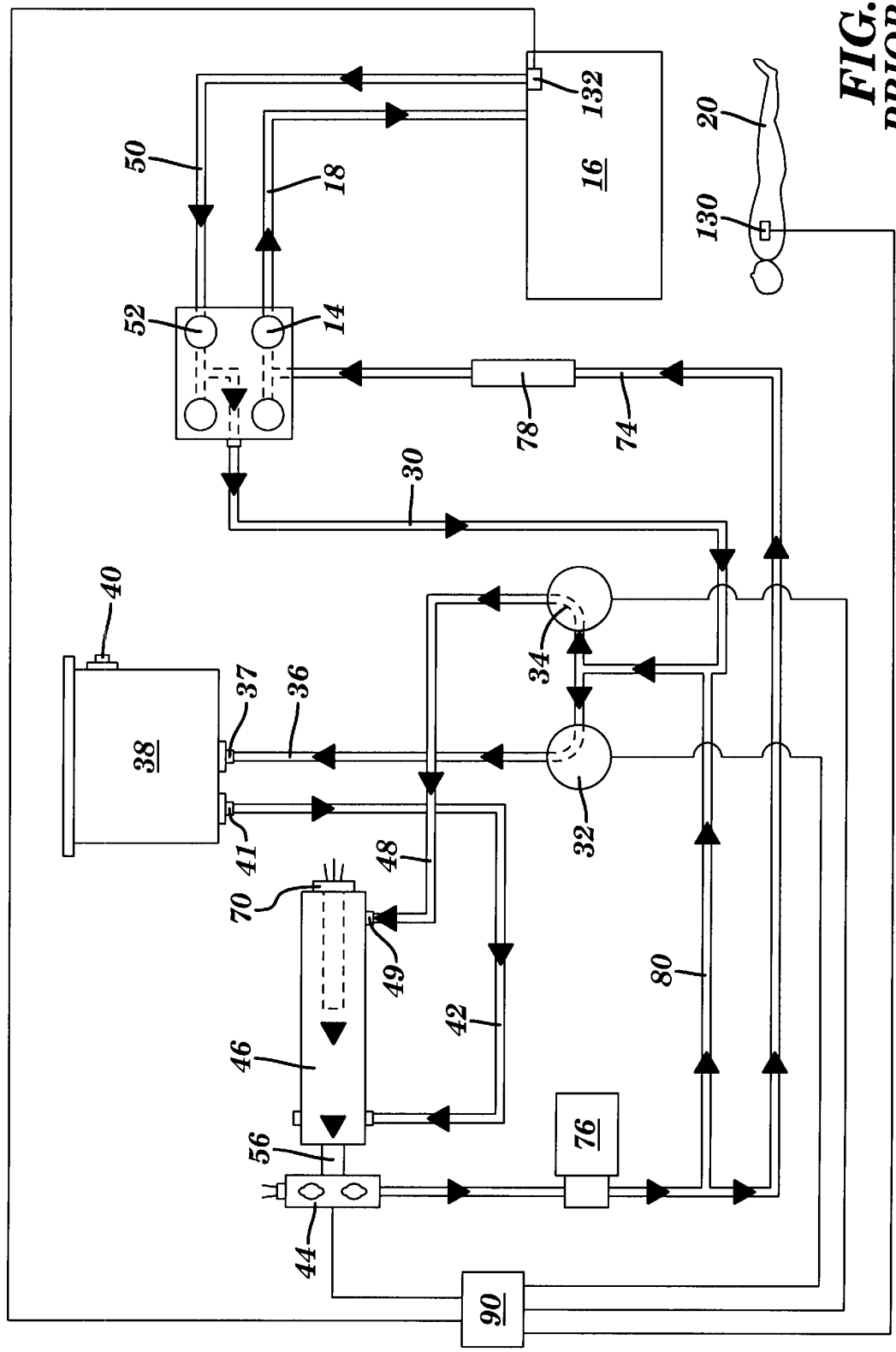
FIG. 1 illustrates a prior art schematic flow diagram of how the MEDI-THERM II® hypo/hyperthermia machine distributes water to and from an Object.
Figure 2:
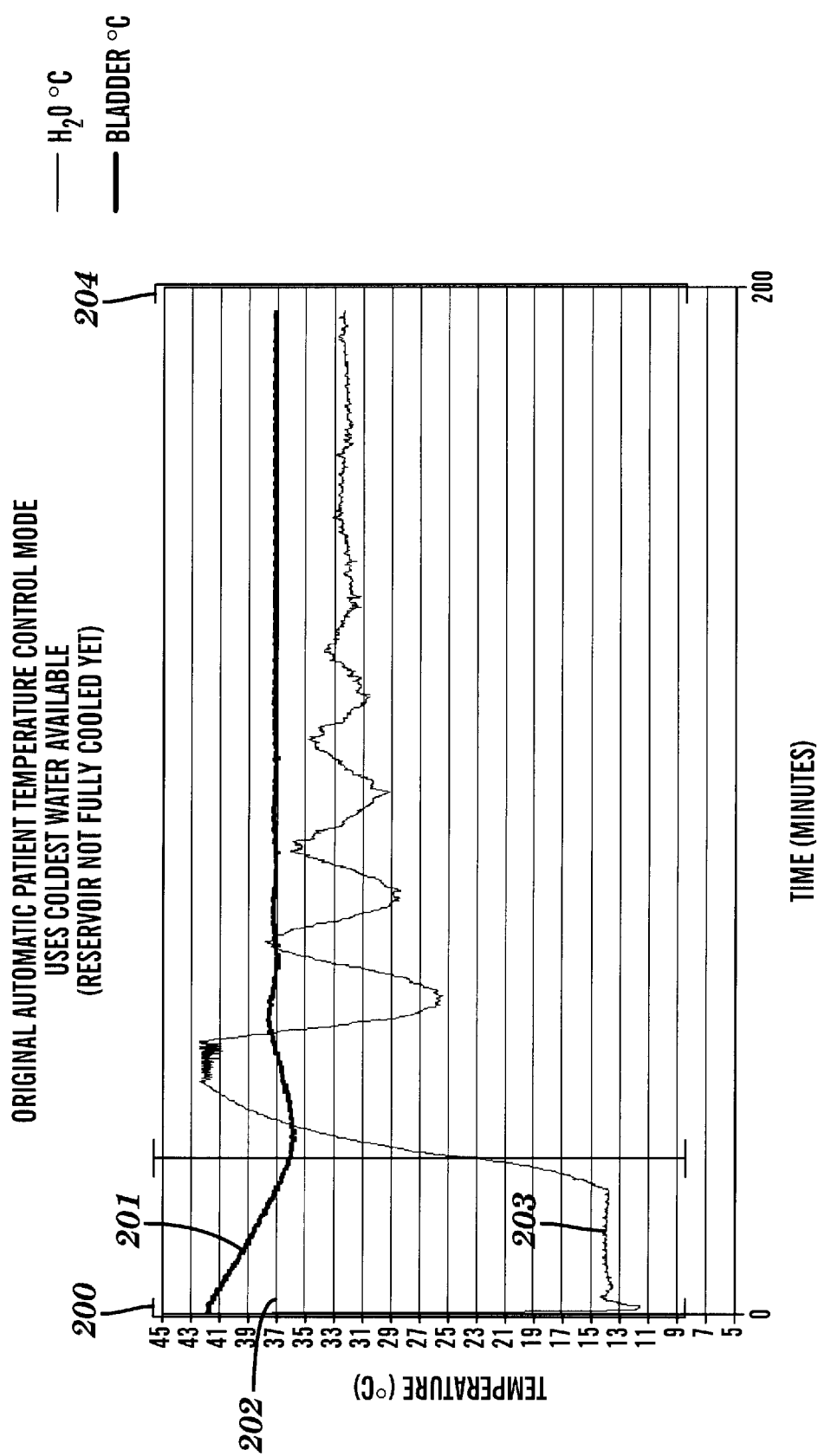
FIG. 2 illustrates a prior art graph of the FIG. 1.
Figure 3:
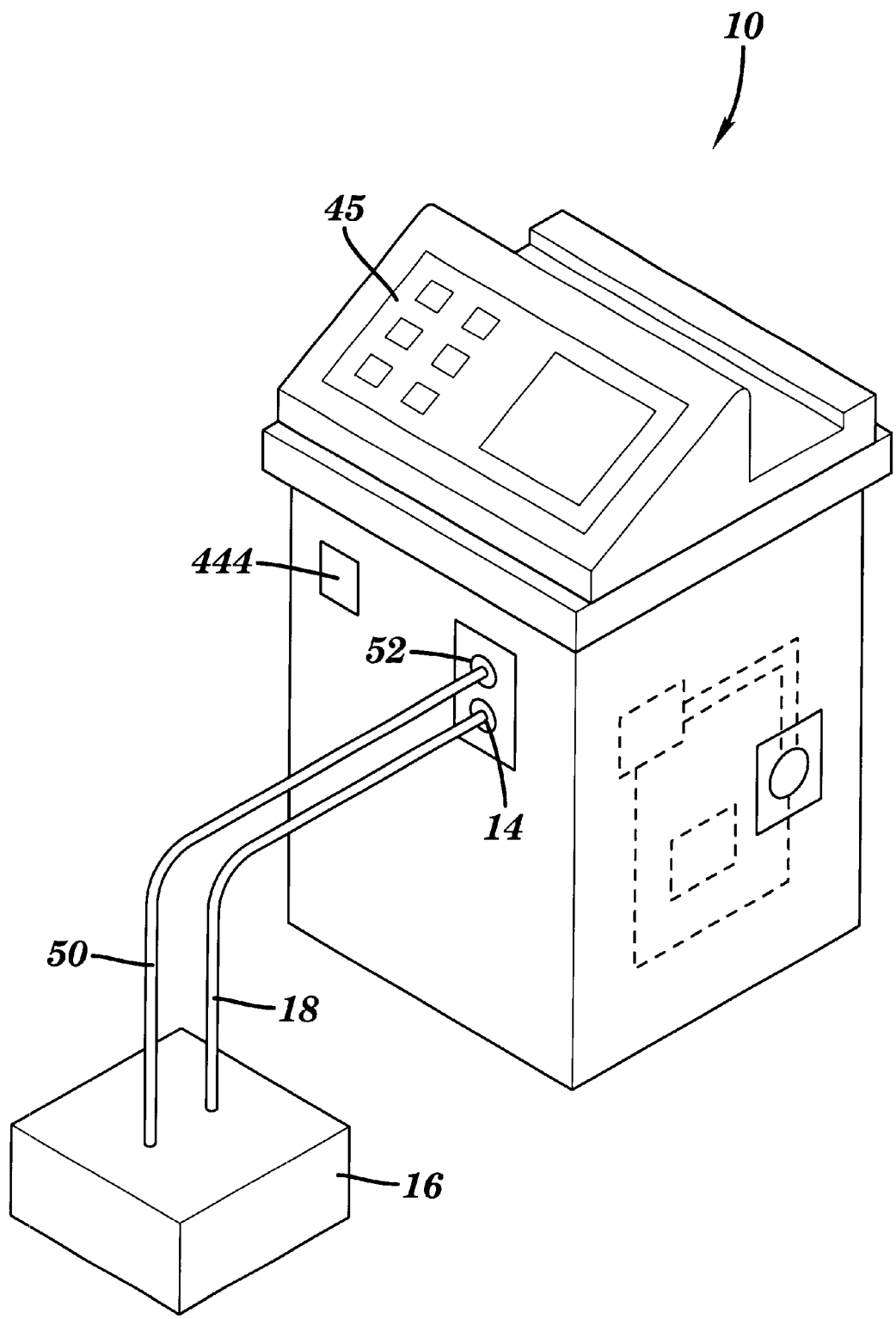
FIG. 3 illustrates the exterior embodiment of the present invention.

One embodiment of the present invention is illustrated in FIG. 3. This embodiment relates to a liquid medium delivery device 10. The exterior of the device 10 has at least one supply outlet 14, a kill switch 444 which can shut down the entire device 10 by conventional interconnections between the various components of device 10, a display/input unit 45, at least one outlet conduit 18, a return conduit 50, a return inlet 52, and an Object 16.

Figure 4:
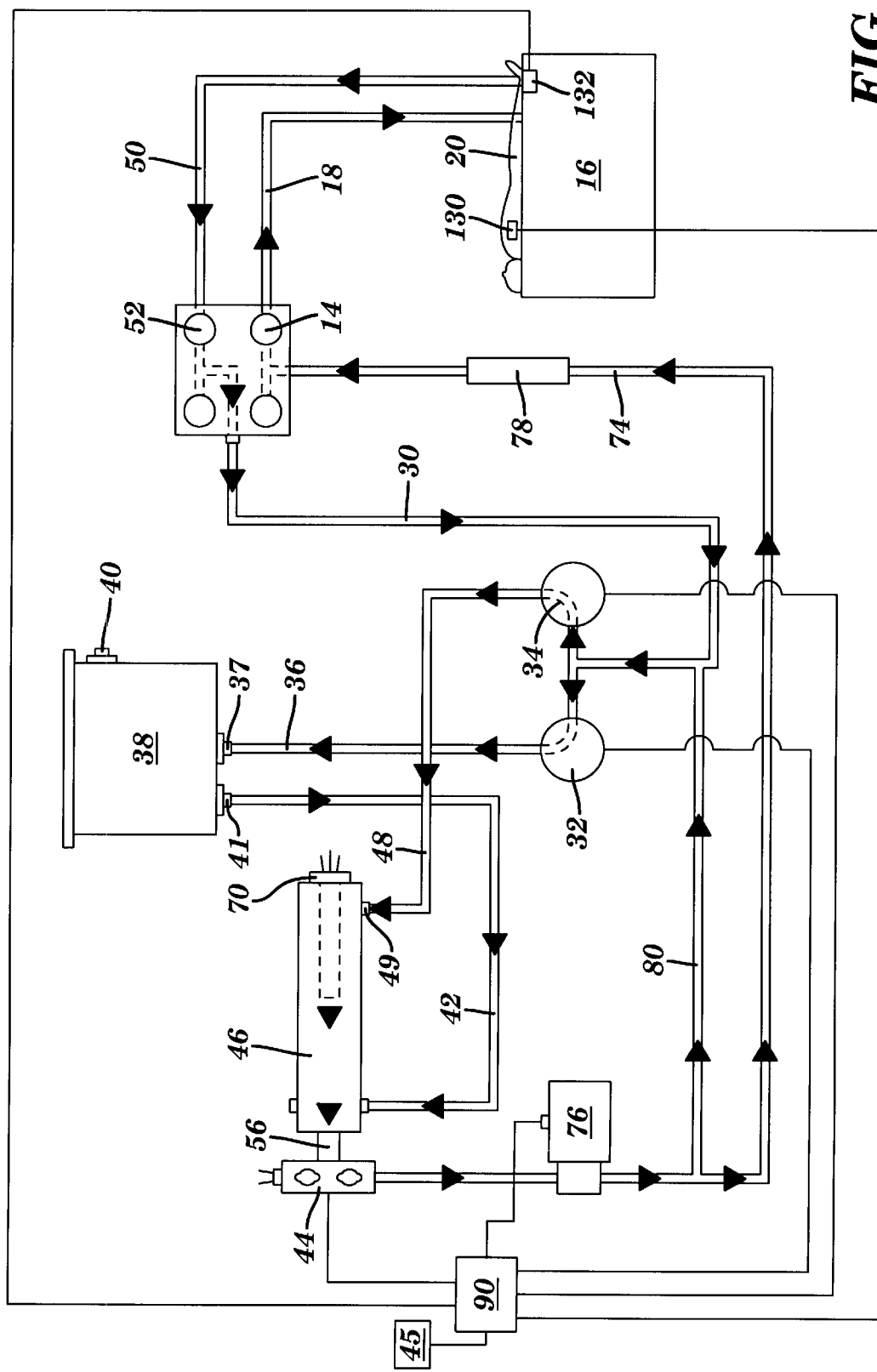
FIG. 4 illustrates a schematic flow diagram of how the present invention distributes a liquid medium to and from an Object

FIG. 4 is a flow diagram of how device 10 distributes the liquid medium. The liquid medium enters device 10 through the return inlet 52. From return inlet 52, the liquid medium traverses through the first conduit 30 to the first solenoid valve 32 for a cold liquid medium or the second solenoid valve 34 for a warm liquid medium.

From the first solenoid 32 which is controlled by a processor unit 90 (to be described later), the liquid medium goes through a second conduit 36 and the first cold inlet 37 of the cold reservoir 38 to the cold reservoir 38. The cold reservoir 38 is a conventional cooling unit that cools a liquid, i.e., a refrigeration system's evaporation or an air conditioner's evaporator. The evaporator in the reservoir maintains a large quantity of fluid at a predetermined temperature normally 4° C. (hereinafter "Cold Medium"). Liquid medium entering the reservoir is cooled by mixing with the liquid medium already within the reservoir. If the cold reservoir 38 overflows, the liquid medium escapes from the device 10 through the overflow outlet 40. The Cold Medium then flows through the cold outlet 41 of the cold reservoir 38 and the third conduit 42 to a manifold 44.

Similarly from the second solenoid 34 which is controlled by the processor unit 90, the liquid medium goes to a hot reservoir 46 through the fourth conduit 48 and the hot inlet port 49 of the hot reservoir 46. The hot reservoir 46 is a conventional heating apparatus that heats the liquid medium (hereinafter "Warm Medium"). The warm Medium flows through the warm outlet 56 of the hot reservoir 46 to the manifold 44.

At the manifold 44, the Warm Medium and the Cold Medium converge. The selection of which liquid medium path is active and its length of time active is controlled via solenoid valves 32 and 34 to attain a desired temperature. The Mixed Medium is drawn through the sixth conduit 74 by the conventional pump 76, to supply outlet 14. A flow switch 78 on the sixth conduit 74 senses whether the Mixed Medium reaches the supply outlet 14. Obviously, when the flow switch 78 is on, the Mixed Medium reaches the supply outlet 14. And when the flow switch 78 is off, the Mixed Medium fails to reach the supply outlet 14. A seventh conduit 80 connects with the first conduit 30, to provide quelling of temperature overshoot when no Object is connected.

When the Mixed Medium reaches the supply outlet 14, the liquid medium is released into the outlet conduit 18 into the Object 16. The Mixed Medium traverses through the Object 16 to the return conduit 50 and into the return inlet 52. And the process is repeated.

The Mixed Medium temperature is altered by the first solenoid valve 32 which controls the intake of the Warm Medium and the second solenoid valve 34 which controls the intake of the Cold Medium. The amount of medium each solenoid valve 32, 34 allows into the manifold 44 depends on the temperature of the mammal 20 and, sometimes depending on the embodiment of the present invention, the temperature of the Mixed Medium in the Object.

The temperature of the mammal 20 is measured by the first conventional temperature sensing device 130 connected to the preselected portion of the mammal 20 and interconnected to the processing unit 90. The measurement from the first temperature sensing device 130 is transmitted to the processing unit 90.

The temperature of the Mixed medium in the Object is measured by the second conventional temperature measuring device 132 placed in the Object, in the supply conduit 18, the supply outlet 14, the manifold 44, or the sixth conduit 74. The measurement from the second temperature measuring device 132 is transmitted to the processing unit 90.

Initially, the processing unit 90 compares the measurement from the first temperature sensing device 130 (hereinafter "First Measurement") to the Set Point Body temperature of the mammal 20 (hereinafter "Set Point Body Temperature"). The processing unit 90 determines the differential and, in return, adjusts the temperature of the Mixed Medium to a preset differential by controlling the solenoid valves 32, 34.

When the First Measurement is above the Set Point Body Temperature, the processing unit 90 controls the first and second solenoid valves 32, 34 to alter the temperature of the Mixed Medium to a predetermined differential from the First Measurement. The predetermined differential ranges from 0.1 to 35 degrees Celsius, and preferably ranges from 5 to 15 degrees Celsius, below the First Measurement.

Figure 5A:
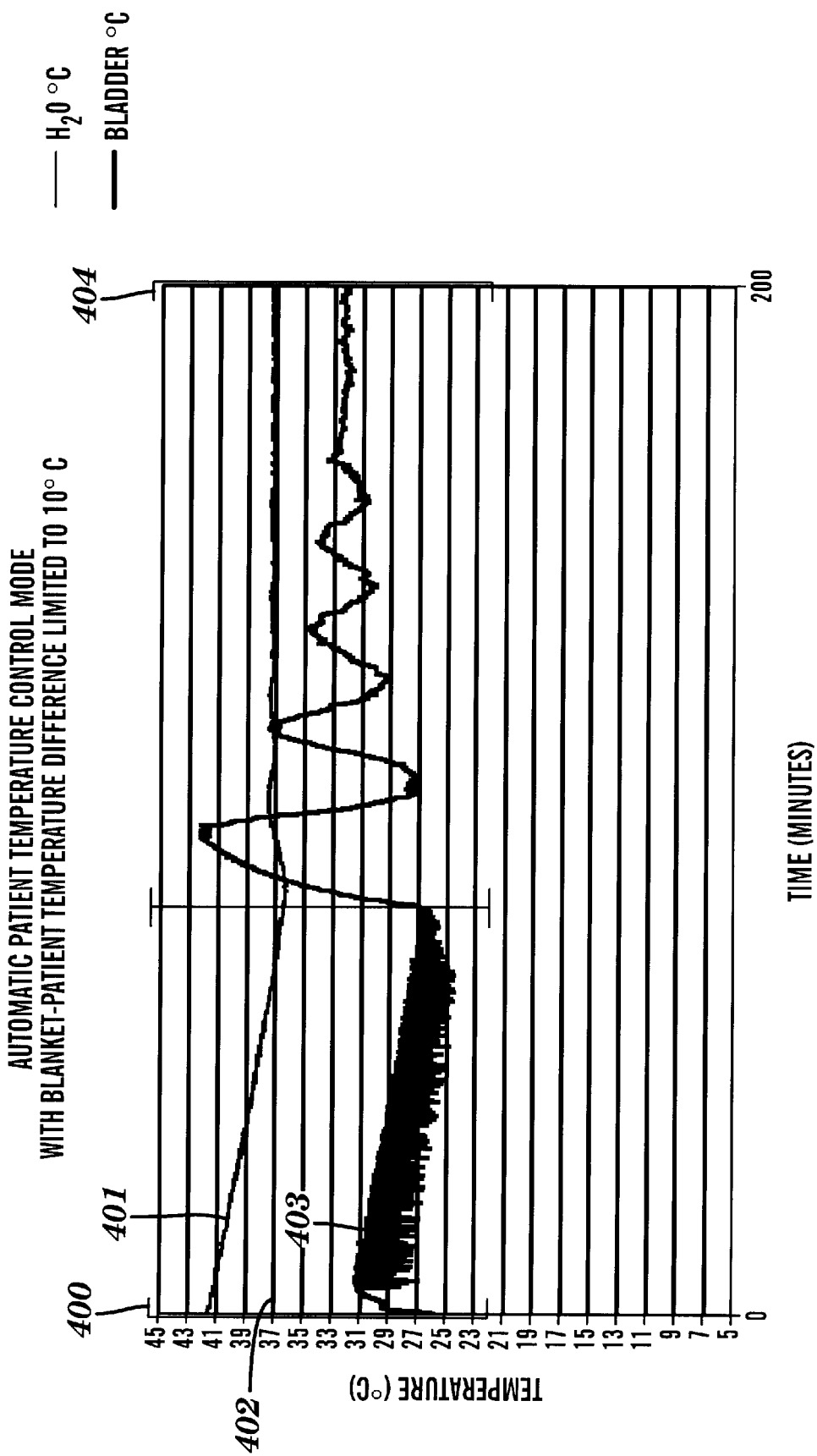
FIGS. 5A, 5B, and 5C illustrate graphs showing the actual temperature of a patient and the temperature of the desired medium applied to the patient over time of the present invention.
Figure 5B:
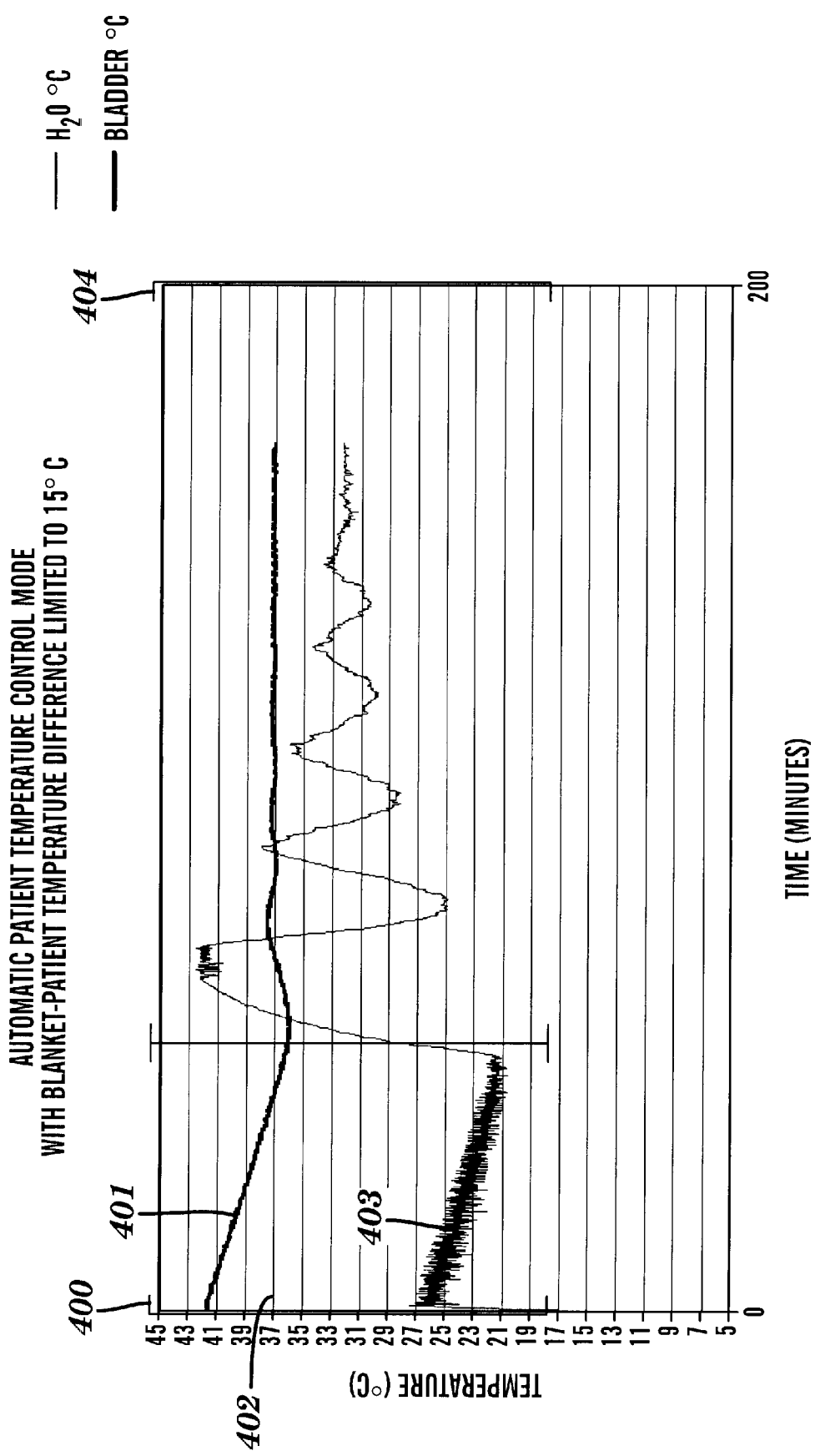

Initially when the First Measurement is above the Set Point Body Temperature, the device 10 applies, by the processing unit 90 controlling the first and second solenoids 32, 34, a Mixed Medium into the Object 16 having a predetermined differential from the First Measurement. The predetermined differential ranges from 0.1 to 35 degrees Celsius, and preferably ranges from 5 to 15 degrees Celsius, below the First Measurement. FIGS. 5a (a 10° C. differential) and 5b (a 15° C. differential) illustrate this design feature in section 400 wherein the temperature of the First Measurement is represented as line 401, the Set Point Body Measurement is represented as line 402, and the Mixed Medium is represented as line 403 at different differentials. Once the First Measurement 401 falls below the Set Point Body Temperature 402, the first and second solenoid valves 32, 34 alter the temperature of the Mixed Medium, to eventually stabilize the patient to the Set Point Body Temperature. See section 404 of FIGS. 5A and B.

Likewise, when the First Measurement is initially below the Set Point Body Temperature, the processing unit 90 controls the first and second solenoid valves 32, 34 to alter the temperature of the Mixed Medium to a pre-set differential from the First Measurement. The pre-set differential ranges from 0.1 to 35 degrees Celsius, and preferably ranges from 5 to 15 degrees Celsius, above the actual temperature, so long as the processing unit 90 does not alter the temperature of the Mixed Medium above a predetermined-maximum temperature. The predetermined-maximum temperature is 0.1 to 10 degrees Celsius, and preferably about 5 degrees Celsius, above the normal temperature of the mammal.

And when the First Measurement is about the Set Point Body Temperature, the processing unit 90 controls the first and second valves 32, 34 to alter the temperature of the Mixed Medium to a temperature which will maintain the First Measurement about the Set Point Body temperature.

The liquid medium can be any liquid that transfers thermal energy to a mammal 20 and wherein the liquid can be readily altered to a Warm Medium or a Cold Medium, like water or water-based solutions.

Alternatively, the liquid medium set forth in the present invention can be substituted by a gaseous medium, like air. When device 10 delivers air instead of a liquid medium, device 10 is altered. Instead of having valves 32, 34, conduits 48, 36, 42, and reservoirs 38, 46, the device 10 has a different temperature and intake system.

Figure 6:
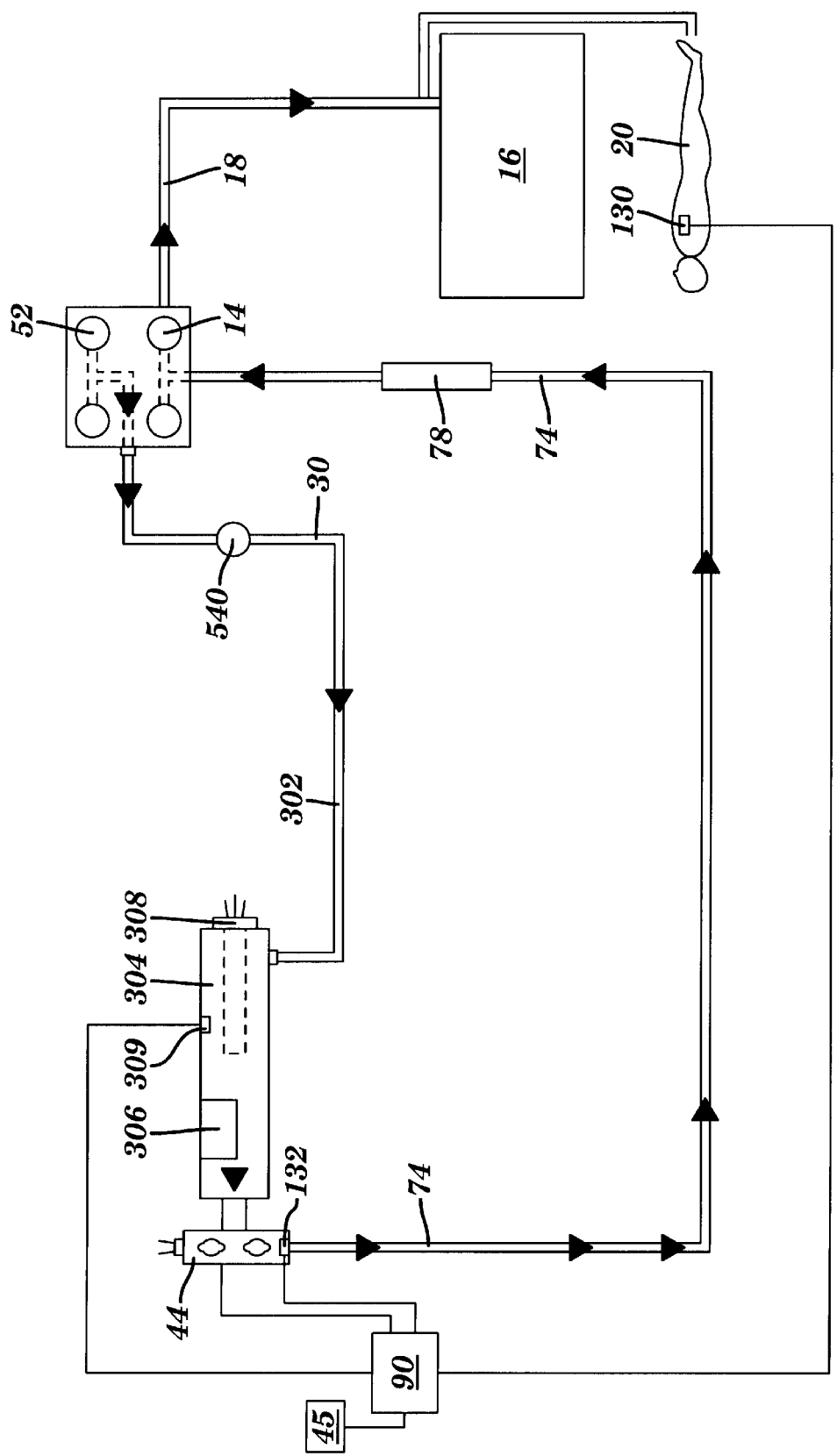
FIG. 6 illustrates an alternative embodiment of FIG. 4.

Turning to FIG. 6, the air is drawn into device 10 through the inlet 52 by a conventional fan 540. From the inlet 52, the air medium traverses through a ninth conduit 302 to a plenum 304. The plenum 304 has a cooling unit 306, like an air conditioner, and a heating unit 308, like a heat pump. The processing unit 90 controls the cooling unit 306 and the heating unit 308 by conventional methods well known to those skilled in the art.

The air then escapes into the manifold 44 and follows route set forth for FIG. 3, except the air does not return to the device 10 from the Object 16. The temperature of the Mixed Medium in the Object 16 is measured by the second conventional temperature measuring device 132 placed in the Object 16, in the supply conduit 18, the supply outlet 14, the sixth conduit 74, the manifold 44 or the plenum 304. The measurement from the second temperature measuring device is transmitted to the processing unit 90.

The processing unit 90, in return, alters the operation of the cooling unit 306 and the heating unit 308 to obtain the desired air temperature.

Figure 7:
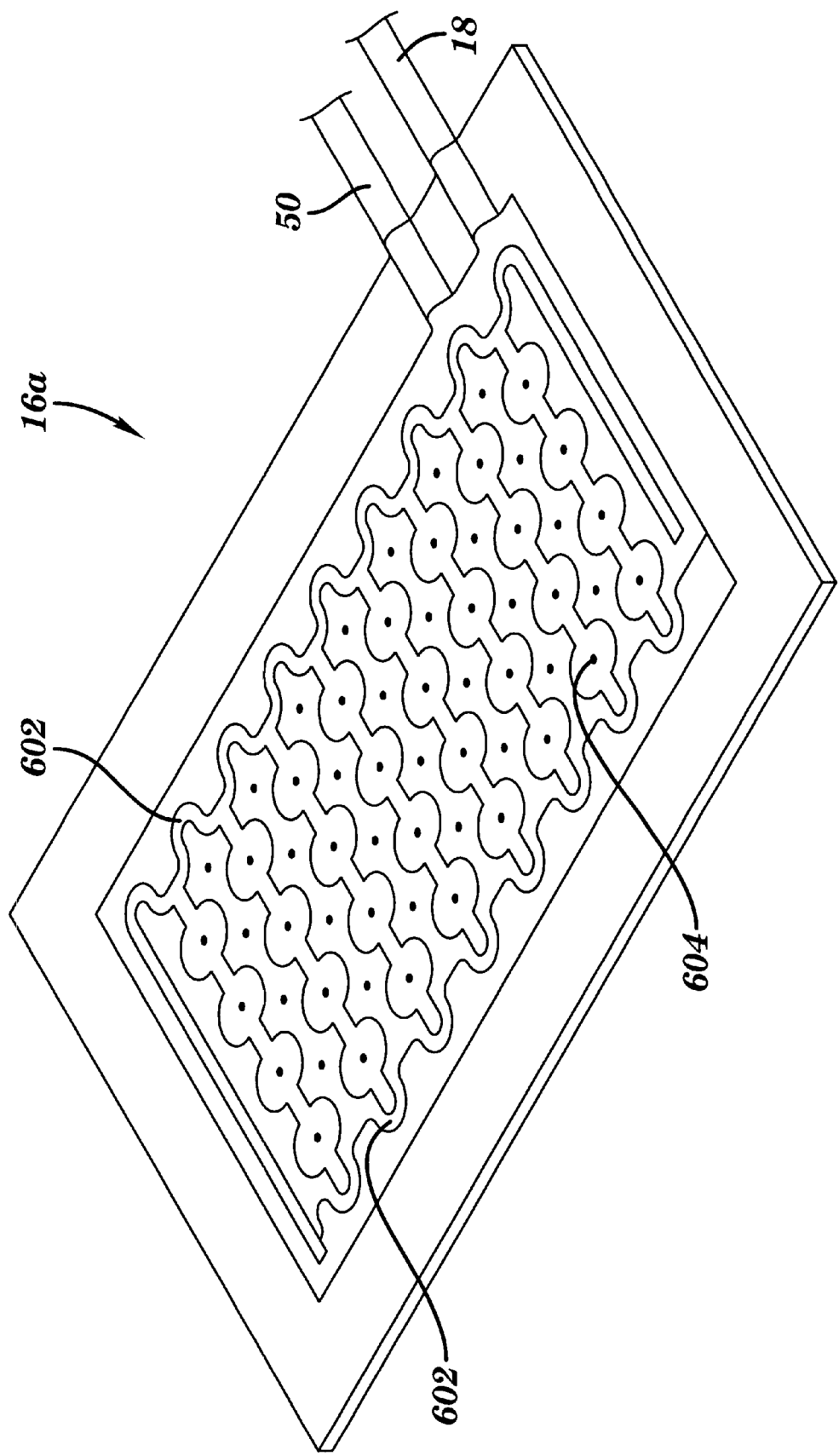
FIG. 7 illustrates an Object, wherein the Object is a blanket having a plurality of channels and a plurality of apertures for directing the desired medium in the direction of the user.
Figure 8:
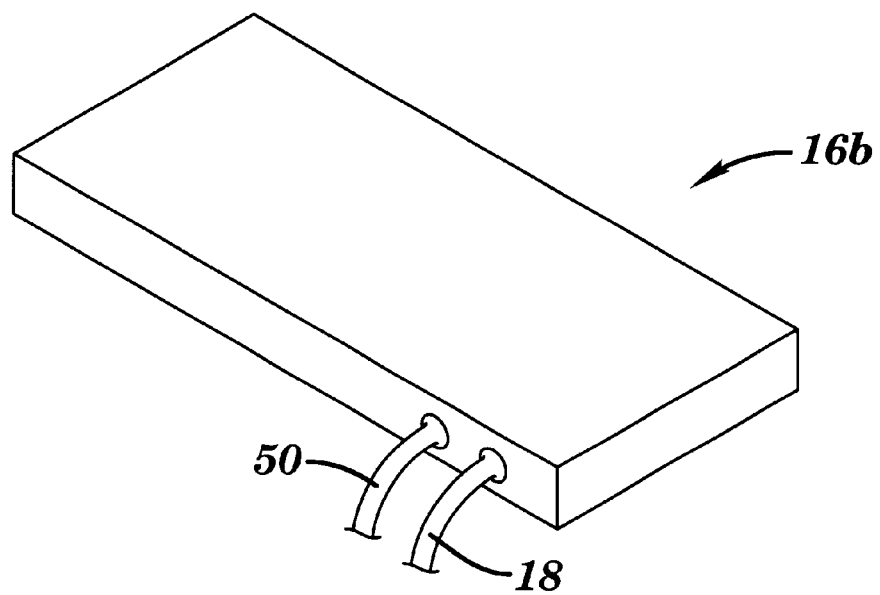
FIG. 8 illustrates an Object, wherein the Object is a mattress.
Figure 9:
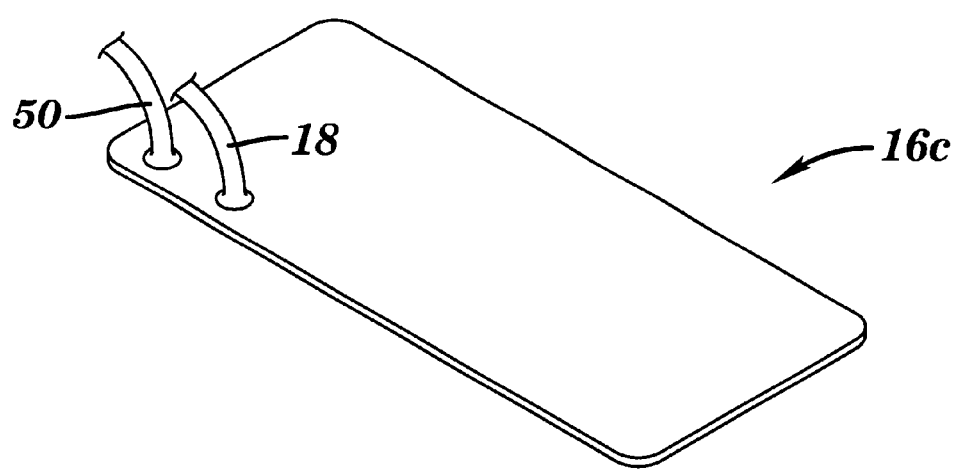
FIG. 9 illustrates an Object, wherein the Object is a mattress pad.

In accordance with the present invention, the Object 16 can be any suitable object, such as a blanket, a mattress, or a mattress pad. Such Objects 16 are shown in FIGS. 7–9. In particular, FIG. 7 shows a blanket 16a having a plurality of channels 602 and a plurality of apertures 604 for directing the desired medium in the direction of the user. Although FIG. 7 shows outlet conduit 18 directing the desired medium into the blanket 600, the outlet conduit 18 may be positioned to direct the desired medium under the blanket 600. Referring to FIG. 8, the Object 16 may be a mattress 16b. Alternatively, the Object 16 may be a mattress pad 16c, as shown in FIG. 9.

In accordance with the present invention, the Object 16 can be any suitable object, such as a blanket, a mattress, or a mattress pad. Such Objects 16 are shown in FIGS. 7–9. In particular, FIG. 7 shows a blamket 16a having a plurality of channels 602 and a plurality of apertures 604 for directing the desired medium in the direction of the user. Although FIG. 7 shows outlet conduit 18 durecting the desired medium into the blanket 600, the outlet conduit 18 may be positioned to direct the desired medium under the blanket 600. Referring to FIG. 8, the Object 16 may be a mattress 16b. Alternatively, the Object 16 may be a mattress pad 16c, as shown in FIG. 9.

Figure 5C:
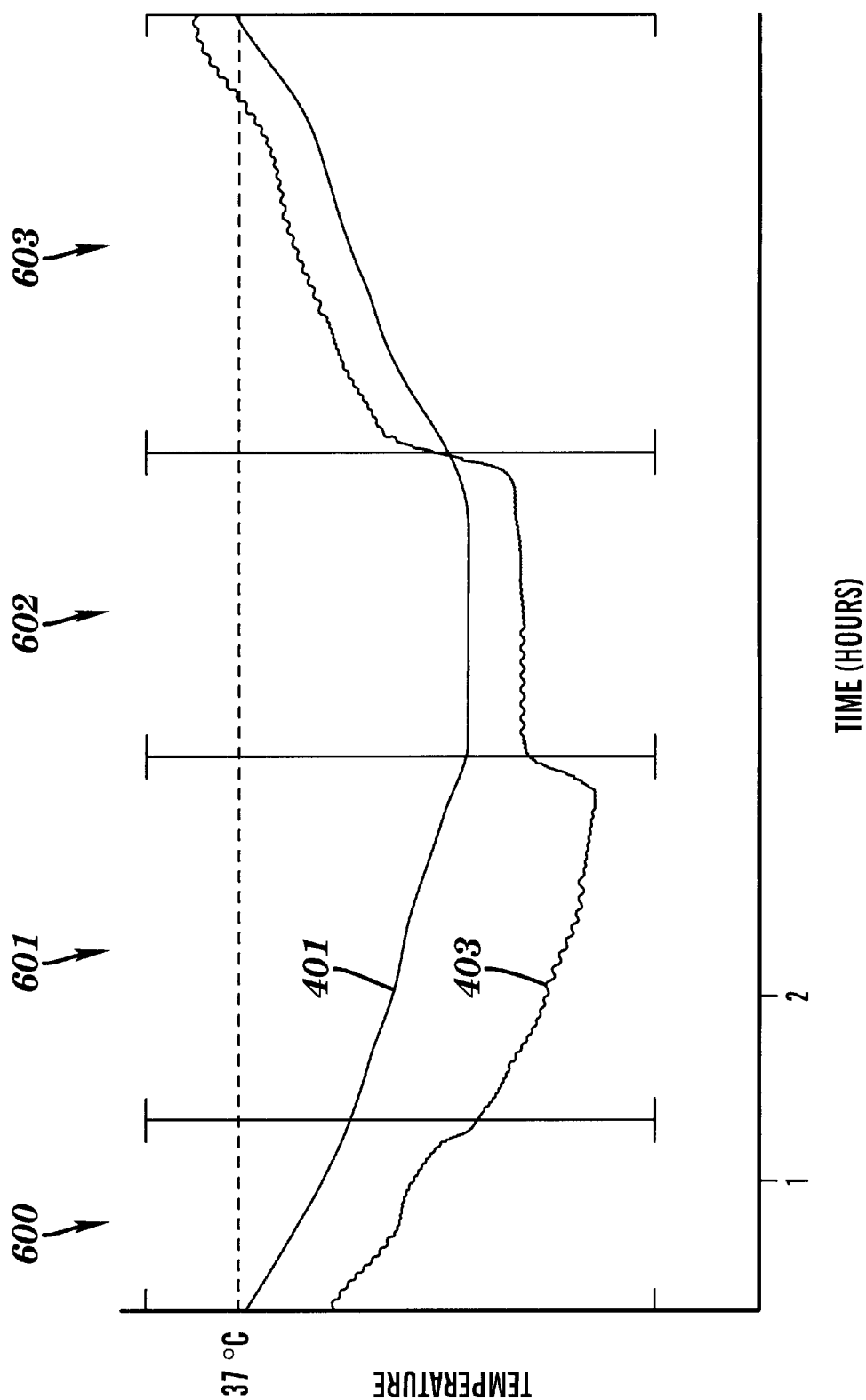

Alternatively, the processing unit 90 can be programmed and/or pre-set to alter the temperature of the Mixed Medium and/or the temperature of the mammal 20 at a set rate. For example, altering the temperature of the Mixed Medium or mammal 16 at 2° C., or any other temperature change, per hour. These changes can occur in time increments, as well. For example, the processing unit 90 can be programmed, as illustrated in FIG. 5c wherein the lines 401 and 403 are defined above, to (1) cool the mammal 16 (or Mixed Medium) to 34° C. at 2° C./hour during a first time period (area 600), (2) cool the mammal 16 (or Mixed Medium) to 32° C. using a 20° C. maximum differential during a second time period (area 601), (3) during a third time frame, the mammal's (or Mixed Medium's) temperature is to be maintained at 32° C.—to maintain this temperature for the mammal the Mixed Medium is at a maximum pre-set differential, i.e., a 10° C. maximum differential from the mammal's temperature—for 1 hour (area 602); and (4) raise the mammals' (or Mixed Medium's) temperature to 37° C., or any other predetermined temperature at a rate of 4° C. per hour (area 603). Obviously, these examples can be used with different temperatures, different differentials, and different, desired rates. By controlling these rates, temperatures, and differentials individually and/or collectively, by manual means of inputting the data into the processing unit 90, automatic means of a pre-programmed rate and/or temperature, or a combination of both means, the processing unit 90 controls the solenoid valves 32, 34, 320 and manifold 44 to distribute the Mixed Medium at the predetermined temperature and/or predetermined rate.

While preferred embodiments of the present invention have been disclosed, it will be appreciated that it is not limited thereto but may be otherwise embodied with the scope of the following claims.

We claim the following:

1. A device for delivering a desired medium at certain temperature ranges for temperature management of a mammal, comprising:

an inlet source receives the desired medium and directs the desired medium to a temperature-control device;

a bio-feedback device measures the mammal's actual temperature, and transmits the measurement to the temperature-control device;

depending on the measurement, the temperature-control device alters the temperature of the desired medium; and an outlet source directs the desired medium to manage the temperature of the mammal;

wherein the mammal is to have its temperature set to a predetermined-desired temperature which is entered into the temperature-control device;

wherein when the actual temperature is above the predetermined-desired temperature, the temperature-control device alters the temperature of the desired medium to a predetermined differential from the actual temperature; and wherein when the actual temperature is below the predetermined-desired temperature, the temperature-control device alters the temperature of the desired medium to a pre-set differential from the actual temperature.

2. The device of claim 1 wherein the desired medium is water.

3. The device of claim 1 wherein the desired medium is air.

4. The device of claim 1 wherein the predetermined differential ranges from 0.1 to 35 degrees Celsius below the actual temperature.

5. The device of claim 1 wherein the predetermined differential ranges from 5 to 15 degrees Celsius below the actual temperature.

6. The device of claim 1 wherein the pre-set differential ranges from 0.1 to 35 degrees Celsius above the actual temperature, so long as the temperature-control device does not alter the temperature of the desired medium above a predetermined-maximum temperature.

7. The device of claim 6 wherein the predetermined-maximum temperature is 0.1 to 10 degrees Celsius above a predetermined-healthy temperature of the mammal.

8. The device of claim 6 wherein the predetermined-maximum temperature is about 5 degrees Celsius above a predetermined-healthy temperature of the mammal.

9. The device of claim 1 wherein the pre-set differential ranges from 5 to 15 degrees Celsius above the actual temperature.

10. The device of claim 1 wherein the temperature-control device is a heat transfer unit with a temperature-measurement instrument.

11. The device of claim 1 wherein the outlet source directs the desired medium into a blanket.

12. The device of claim 11 wherein the blanket has a plurality of channels.

13. The device of claim 11 wherein the blanket has a plurality of apertures directing the desired medium in the direction of the mammal.

14. The device of claim 1 wherein the outlet source directs the desired medium under a blanket.

15. The device of claim 1 wherein the outlet source directs the desired medium to a mattress.

16. The device of claim 1 wherein the outlet source directs the desired medium to a mattress pad.

17. The device of claim 1 wherein the temperature-control device can alter the temperature of the desired medium at a predetermined rate.

18. The device of claim 1 wherein the predetermined-desired temperature is selected from the group consisting of a temperature below the mammal's normal temperature, the mammal's normal temperature, and a temperature above the mammal's normal temperature.

19. A device for delivering a desired medium within a desired temperature range for temperature management of a mammal, comprising:

an inlet source receives the desired medium and directs the desired medium to a temperature-control device;

a bio-feedback device measures the mammal's actual temperature, and transmits the measurement to the temperature-control device; depending on the measurement, the temperature-control device alters the temperature of the desired medium; and an outlet source directs the desired medium to manage the temperature of the mammal;

wherein the mammal has a predetermined-healthy temperature which is entered into the temperature-control device;

wherein when the actual temperature is above the predetermined-healthy temperature, the temperature-control device alters the temperature of the desired medium to a predetermined differential from the actual temperature;

wherein when the actual temperature is below the predetermined-healthy temperature, the temperature-control device alters the temperature of the desired medium to a pre-set differential from the actual temperature; and wherein when the actual temperature is about the predetermined-healthy temperature, the temperature-control device alters the temperature of the desired medium to maintain the actual temperature.

20. The device of claim 19 wherein the desired medium is water.

21. The device of claim 19 wherein the desired medium is air.

22. The device of claim 19 wherein the predetermined differential ranges from 0.1 to 35 degrees Celsius below the actual temperature.

23. The device of claim 19 wherein the predetermined differential ranges from 5 to 15 degrees Celsius below the actual temperature.

24. The device of claim 19 wherein the pre-set differential ranges from 0.1 to 35 degrees Celsius above the actual temperature, so long as the temperature-control device does not alter the temperature of the desired medium above a predetermined-maximum temperature.

25. The device of claim 24 wherein the predetermined-maximum temperature is 0.1 to 10 degrees Celsius above the predetermined-healthy temperature.

26. The device of claim 24 wherein the predetermined-maximum temperature is about 5 degrees Celsius above the predetermined-healthy temperature.

27. The device of claim 19 wherein the pre-set differential ranges from 5 to 15 degrees Celsius above the actual temperature.

28. The device of claim 19 wherein the preselected differential is from 0.01 to 5 degrees Celsius above and below the predetermined-healthy temperature.

29. The device of claim 19 wherein the temperature-control device is a heat transfer unit with a temperature-measurement instrument.

30. The device of claim 19 wherein the outlet source directs the desired medium into a blanket.

31. The device of claim 30 wherein the blanket has a plurality of channels.

32. The device of claim 30 wherein the blanket has a plurality of apertures directing the desired medium in the direction of the mammal.

33. The device of claim 19 wherein the outlet source directs the desired medium under a blanket.

34. The device of claim 19 wherein the outlet source directs the desired medium to a mattress.

35. The device of claim 19 wherein the outlet source directs the desired medium to a mattress pad.

36. The device of claim 19 wherein the temperature-control device can alter the temperature of the desired medium at a predetermined rate.

37. A method of using a device for delivering a desired medium within a selected temperature range for temperature management of a mammal, comprising following steps:
    directing the desired medium into an inlet source and a temperature-control device;
    measuring the mammal's actual temperature with a bio-feedback device, and transmitting the measurement to the temperature-control device;
    depending on the measurement, altering the temperature of the desired medium with the temperature-control device;
    directing the desired medium through an outlet source to manage the temperature of the mammal;
    wherein the mammal is to have its temperature adjusted to a predetermined-desired temperature which is entered into the temperature-control device;
    wherein when the actual temperature is above the predetermined-desired temperature, the temperature-control device alters the temperature of the desired medium to a predetermined differential from the actual temperature; and
    wherein when the actual temperature is below the predetermined-desired temperature, the temperature-control device alters the temperature of the desired medium to a pre-set differential from the actual temperature.

38. The method of claim 37 wherein the desired medium is water.

39. The method of claim 37 wherein the desired medium is air.

40. The method of claim 37 wherein the predetermined differential ranges from 0.1 to 35 degrees Celsius below the actual temperature.

41. The method of claim 37 wherein the predetermined differential ranges from 5 to 15 degrees Celsius below the actual temperature.

42. The method of claim 37 wherein the pre-set differential ranges from 0.1 to 35 degrees Celsius above the actual temperature, so long as the temperature-control device does not alter the temperature of the desired medium above a predetermined-maximum temperature.

43. The method of claim 42 wherein the predetermined-maximum temperature is 0.1 to 19 degrees Celsius above a predetermined-healthy temperature of the mammal.

44. The method of claim 42 wherein the predetermined-maximum temperature is about 5 degrees Celsius above a predetermined-healthy temperature of the mammal.

45. The method of claim 37 wherein the pre-set differential ranges from 5 to 15 degrees Celsius above the actual temperature.

46. The method of claim 37 wherein the preselected differential is from 0.01 to 5 degrees Celsius above and below the predetermined-healthy temperature.

47. The method of claim 37 wherein the temperature-control device is a heat transfer unit with a temperature-measurement instrument.

48. The method of claim 37 wherein the outlet source directs the desired medium into a blanket.

49. The method of claim 48 wherein the blanket has a plurality of channels.

50. The method of claim 48 wherein the blanket has a plurality of apertures directing the desired medium in the direction of the mammal.

51. The method of claim 37 wherein the outlet source directs the desired medium under a blanket.

52. The method of claim 37 wherein the outlet source directs the desired medium to a mattress.

53. The method of claim 37 wherein the outlet source directs the desired medium to a mattress pad.

54. The method of claim 37 wherein the temperature-control device can alter the temperature of the desired medium at a predetermined rate.

55. The method of claim 37 wherein the predetermined-desired temperature is selected from the group consisting of a temperature below the mammal's normal temperature, the mammal's normal temperature, and a temperature above the mammal's normal temperature.

56. A device for delivering a desired medium at certain temperature ranges for temperature management of a mammal, comprising:
    an inlet source receives the desired medium and directs the desired medium to a temperature-control device;
    a bio-feedback device measures the mammal's actual temperature, and transmits the measurement to the temperature-control device;
    depending on the measurement, the temperature-control device alters the temperature of the desired medium; and
    an outlet source directs the desired medium to manage the temperature of the mammal;
    wherein the mammal is to have its temperature set to a predetermined-desired temperature which is entered into the temperature-control device;
    wherein when the actual temperature is above the predetermined-desired temperature, the temperature-control device alters the temperature of the desired medium at a predetermined rate; and
    wherein when the actual temperature is below the predetermined-desired temperature, the temperature-control device alters the temperature of the desired medium at a predetermined rate.

57. The device of claim 56 wherein the desired medium is water.

58. The device of claim 56 wherein the desired medium is air.

59. The device of claim 56 wherein the predetermined differential ranges from 0.1 to 35 degrees Celsius below the actual temperature.

60. The device of claim 56 wherein the predetermined differential ranges from 5 to 15 degrees Celsius below the actual temperature.

61. The device of claim 56 wherein the pre-set differential ranges from 0.1 to 35 degrees Celsius above the actual temperature, so long as the temperature-control device does not alter the temperature of the desired medium above a predetermined-maximum temperature.

62. The device of claim 61 wherein the predetermined-maximum temperature is 0.1 to 10 degrees Celsius above a predetermined-healthy temperature of the mammal.

63. The device of claim 61 wherein the predetermined-maximum temperature is about 5 degrees Celsius above a predetermined-healthy temperature of the mammal.

64. The device of claim 56 wherein the pre-set differential ranges from 5 to 15 degrees Celsius above the actual temperature.

65. The device of claim 56 wherein the temperature-control device alters the temperature of the desired medium to a pre-set differential from the actual temperature.

66. The device of claim 56 wherein the blanket has a plurality of channels.

67. The device of claim 56 wherein the blanket has a plurality of apertures directing the desired medium in the direction of the mammal.

68. The device of claim 56 wherein the outlet source directs the desired medium under a blanket.

69. The device of claim 56 wherein the outlet source directs the desired medium to a mattress.

70. The device of claim 56 wherein the outlet source directs the desired medium to a mattress pad.

71. The device of claim 56 wherein the temperature-control device is a heat transfer unit with a temperature-measurement instrument.

72. The device of claim 56 wherein the outlet source directs the desired medium into a blanket.

73. A device for delivering a desired medium at certain temperature ranges for temperature management of a mammal, comprising:

an inlet source receives the desired medium and directs the desired medium to a temperature-control device;

a bio-feedback device measures the mammal's actual temperature, and transmits the measurement to the temperature-control device;

depending on the measurement, the temperature-control device alters the temperature of the desired medium; and an outlet source directs the desired medium to manage the temperature of the mammal;

wherein the mammal is to have its temperature set to a predetermined-desired temperature which is entered into the temperature-control device;

wherein when the actual temperature is above the predetermined-desired temperature, the temperature-control device alters the temperature of the mammal at a predetermined rate; and wherein when the actual temperature is below the predetermined-desired temperature, the temperature-control device alters the temperature of the mammal at a predetermined rate.

74. The device of claim 73 wherein the desired medium is water.

75. The device of claim 73 wherein the desired medium is air.

76. The device of claim 73 wherein the predetermined rate ranges from 0.1 to 25 degrees Celsius per hour.

77. The device of claim 73 wherein the predetermined rate ranges from 1 to 15 degrees Celsius per hour.

78. The device of claim 73 wherein the temperature-control device is a heat transfer unit with a temperature-measurement instrument.

79. The device of claim 78 wherein the predetermined-maximum temperature is 0.1 to 10 degrees Celsius above a predetermined-healthy temperature of the mammal.

80. The device of claim 78 wherein the predetermined-maximum temperature is about 5 degrees Celsius above a predetermined-healthy temperature of the mammal.

81. The device of claim 73 wherein the outlet source directs the desired medium into a blanket.

82. The device of claim 73 wherein the temperature-control device alters the temperature of the desired medium to a pre-set differential from the actual temperature.

83. The device of claim 73 wherein the predetermined-desired temperature is selected from the group consisting of a temperature below the mammal's normal temperature, the mammal's normal temperature, and a temperature above the mammal's normal temperature.

84. The device of claim 73 wherein the blanket has a plurality of channels.

85. The device of claim 73 wherein the blanket has a plurality of apertures directing the desired medium in the direction of the mammal.

86. The device of claim 73 wherein the outlet source directs the desired medium under a blanket.

87. The device of claim 73 wherein the outlet source directs the desired medium to a mattress.

88. The device of claim 73 wherein the outlet source directs the desired medium to a mattress pad.

89. A device for delivering a medium within a predetermined temperature range for temperature management of a user comprising:

a temperature control device having an inlet for receiving a medium and an outlet for directing the medium to a user, and a bio-feedback device, wherein the bio-feedback device transmits the user's actual temperature to the temperature-control device and wherein the temperature-control device alters the temperature of the medium to a predetermined differential, the predetermined differential being limited by a maximum permitted differential throughout a range determined by the user's actual temperature.

90. The device according to claim 89 wherein the maximum permitted differential is 35° C. above or below the user's actual temperature.

91. The device according to claim 90 wherein the maximum permitted differential is 15° C. above or below the user's actual temperature.

92. The device according to claim 89 wherein the temperature control device does not alter the temperature of the medium above a predetermined maximum temperature.

93. The device according to claim 92 wherein the predetermined maximum temperature is 0.1° C. to 10° C. above a predetermined healthy temperature of the user.

94. The device according to claim 93 wherein the predetermined maximum temperature is about 5° C. above the predetermined healthy temperature of the user.

95. The device according to claim 89 wherein the medium is water.

96. The device according to claim 89 wherein the medium is air.

97. The device according to claim 89 wherein the outlet directs the medium into a blanket.

98. The device according to claim 89 wherein the outlet directs the medium under a blanket.

99. The device according to claim 89 wherein the outlet directs the medium to a mattress.

100. The device according to claim 89 wherein the outlet directs the medium to a mattress pad.

101. The device according to claim 89 wherein the temperature control device can alter the temperature of the medium at a predetermined rate.

102. A device for delivering a medium at a predetermined rate for temperature management comprising:

a temperature control device having an inlet for receiving a medium and an outlet for directing the medium to a user, and a bio-feedback device, wherein the bio-feedback device transmits the user's actual temperature to the temperature control device and wherein the temperature control device alters the temperature of the medium at a predetermined rate based on the user's actual temperature.

103. The device according to claim 102 wherein the predetermined rate ranges from 0.1° C. to 25° C. per hour.

104. The device according to claim 103 wherein the predetermined rate ranges from 1° C. to 15° C. per hour.

105. The device according to claim 102 wherein the medium is water.

106. The device according to claim 102 wherein the medium is air.

107. The device according to claim 102 wherein the outlet directs the medium into a blanket.

108. The device according to claim 102 wherein the outlet directs the medium under a blanket.

109. The device according to claim 102 wherein the outlet directs the medium to a mattress.

110. The device according to claim 102 wherein the outlet directs the medium to a mattress pad.

111. A method of temperature management comprising:
  directing a medium into an inlet of a temperature control device;
  measuring an actual temperature of a user;
  transmitting the actual temperature to the temperature control device, wherein the temperature control device alters the temperature of the medium to a predetermined differential, the predetermined differential being limited by a maximum permitted differential throughout a range determined by the user's actual temperature to produce temperature altered medium; and
  directing the temperature-altered medium to the user through an outlet in the temperature control device.

112. The method according to claim 111 wherein the maximum permitted differential is 35° C. above or below the user's actual temperature.

113. The method according to claim 112 wherein the maximum permitted differential is 15° C. above or below the user's actual temperature.

114. The method according to claim 111 wherein the temperature control device does not alter the temperature of the medium above a predetermined maximum temperature.

115. The method according to claim 114 wherein the predetermined maximum temperature is 0.1° C. to 10° C. above a predetermined healthy temperature of the user.

116. The method according to claim 115 wherein the predetermined maximum temperature is about 5° C. above the predetermined healthy temperature of the user.

117. The method according to claim 111 wherein the medium is water.

118. The method according to claim 111 wherein the medium is air.

119. The method according to claim 111 wherein directing the temperature-altered medium comprises directing the temperature-altered medium into a blanket.

120. The method according to claim 111 wherein directing the temperature-altered medium comprises directing the temperature-altered medium under a blanket.

121. The method according to claim 111 wherein directing the temperature-altered medium comprises directing the temperature-altered medium to a mattress.

122. The method according to claim 111 wherein directing the temperature-altered medium comprises directing the temperature-altered medium to a mattress pad.

123. A method of temperature management comprising:
  directing a medium into an inlet of a temperature control device;
  measuring an actual temperature of a user;
  transmitting the actual temperature to the temperature control device, wherein the temperature control device alters the temperature of the medium at a predetermined rate based on the user's actual temperature to produce temperature-altered medium; and
  directing the temperature-altered medium to the user through an outlet in the temperature control device.

124. The method according to claim 123 wherein the predetermined rate ranges from 0.1° C. to 25° C. per hour.

125. The method according to claim 124 wherein the predetermined rate ranges from 1° C. to 15° C. per hour.

126. The method according to claim 123 wherein the temperature control device does not alter the temperature of the medium above a predetermined maximum temperature.

127. The method according to claim 126 wherein the predetermined maximum temperature is 0.1° C. to 10° C. above a predetermined healthy temperature of the user.

128. The method according to claim 127 wherein the predetermined maximum temperature is about 5° C. above the predetermined healthy temperature of the user.

129. The method according to claim 123 wherein the medium is water.

130. The method according to claim 123 wherein the medium is air.

131. The method according to claim 123 wherein directing the temperature-altered medium comprises directing the temperature-altered medium into a blanket.

132. The method according to claim 123 wherein directing the temperature-altered medium comprises directing the temperature-altered medium under a blanket.

133. The method according to claim 123 wherein directing the temperature-altered medium comprises directing the temperature-altered medium to a mattress.

134. The method according to claim 123 wherein directing the temperature-altered medium comprises directing the temperature-altered medium to a mattress pad.

* * * * *

(12) INTER PARTES REEXAMINATION CERTIFICATE (0170th)
United States Patent
Stewart et al.

(10) Number: US 6,517,510 C1
(45) Certificate Issued: Jul. 13, 2010

(54) AUTOMATIC PATIENT CONTROL DEVICE

(75) Inventors: Thomas P. Stewart, Orchard Park, NY (US); Hermann K. Pohl, Orchard Park, NY (US)

(73) Assignee: Gaymar Industries, Inc., Orchard Park, NY (US)

Reexamination Request:
No. 95/000,385, Jul. 31, 2008

Reexamination Certificate for:
Patent No.: 6,517,510
Issued: Feb. 11, 2003
Appl. No.: 09/603,777
Filed: Jun. 26, 2000

(51) Int. Cl.
*A61M 01/00* (2006.01)

(52) U.S. Cl. .................. 604/31; 604/6.11; 604/6.13; 604/23; 604/27; 604/30; 604/113; 604/114; 604/131; 604/151; 604/28; 604/500; 417/207

(58) Field of Classification Search .................. None
See application file for complete search history.

(56) References Cited

U.S. PATENT DOCUMENTS

| | | | |
|---|---|---|---|
| 3,007,473 A | * | 11/1961 | Jackson et al. .............. 607/104 |
| 3,074,410 A | | 1/1963 | Foster |
| 3,338,233 A | | 8/1967 | Grosholz et al. |
| 3,385,958 A | | 5/1968 | Lauck, III |
| 3,507,321 A | | 4/1970 | Palma |
| 3,744,555 A | | 7/1973 | Fletcher et al. |
| 4,034,740 A | | 7/1977 | Atherton et al. |
| 4,184,537 A | | 1/1980 | Sauder |
| 4,277,670 A | | 7/1981 | Mori et al. |
| 4,305,388 A | | 12/1981 | Brisson |
| 4,572,188 A | | 2/1986 | Augustine et al. |
| 4,633,062 A | | 12/1986 | Nishida et al. |
| 4,656,334 A | | 4/1987 | Endo et al. |
| 4,744,372 A | | 5/1988 | Kikuchi et al. |
| 4,884,304 A | | 12/1989 | Elkins |
| 5,008,515 A | | 4/1991 | McCormack |
| 5,033,136 A | | 7/1991 | Elkins |
| 5,062,432 A | | 11/1991 | James et al. |
| 5,073,688 A | | 12/1991 | McCormack |
| 5,097,829 A | * | 3/1992 | Quisenberry ................ 607/105 |
| 5,162,038 A | | 11/1992 | Wilker |
| 5,292,347 A | | 3/1994 | Pompei |
| 5,363,663 A | | 11/1994 | Chen |
| 5,486,204 A | | 1/1996 | Clifton |
| 5,609,619 A | | 3/1997 | Pompei |
| 5,817,147 A | | 10/1998 | Wolf |
| 5,871,526 A | | 2/1999 | Gibbs et al. |
| 5,948,303 A | | 9/1999 | Larson |
| 5,980,561 A | | 11/1999 | Kolen et al. |
| 6,117,164 A | | 9/2000 | Gildersleeve et al. |
| 6,188,930 B1 | | 2/2001 | Carson |
| 6,228,106 B1 | | 5/2001 | Simbruner et al. |
| 6,245,094 B1 | | 6/2001 | Pompei |
| 6,551,347 B1 | | 4/2003 | Elkins |
| 6,579,496 B1 | | 6/2003 | Fausset et al. |
| 6,656,208 B2 | | 12/2003 | Grahn et al. |
| 6,749,624 B2 | | 6/2004 | Knowlton |
| 6,827,898 B1 | | 12/2004 | Fausset et al. |
| 7,001,417 B2 | | 2/2006 | Elkins |
| 2002/0026226 A1 | | 2/2002 | Ein |

FOREIGN PATENT DOCUMENTS

WO  WO-97/25011 A1  7/1997

OTHER PUBLICATIONS

Caruso, Cooling Effects and Comfort of Four Cooling Blanket Temperatures in Humans with Fever, Mar.–Apr.–1992, Nursing Research vol. 41 No. 2 pp. 213–217.*

(Continued)

*Primary Examiner*—Glenn K. Dawson

(57) ABSTRACT

The present invention relates to regulating the temperature of a desired medium that is applied to the exterior surface of a mammal. These devices have been used in the past but not with the ability to control the temperature of the desired medium in a predetermined ratio to the temperature of the mammal. With such control, the present invention decreases the change of discomforting the patient when the patient's temperature is being brought to a set point temperature body temperature.

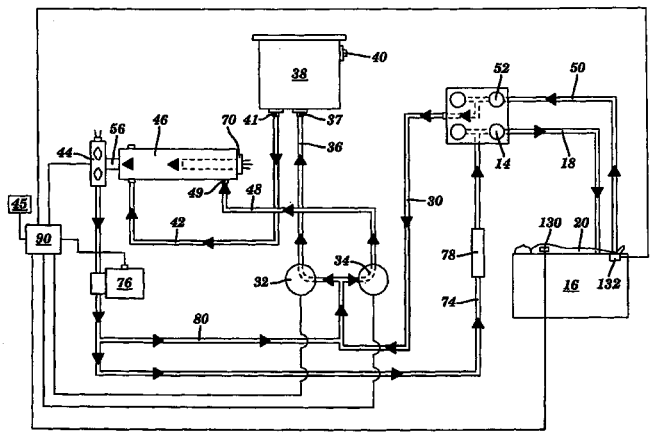

OTHER PUBLICATIONS

Hubbard, R.W., et al., Rapid Hypothermia Subsequent to Oral Nicotinic Acid Ingestion and Immersion in Warm (30° C) Water, Amer Jrnl of Emerg Med, vol6 No. 3, p. 316–17, May 1988, USA.*

Boggs, R.L. and Woolridge–King, M., editors, AACN Procedure Manual For Critical Care—3rd Edition, W.B. Saunders Co., p. 443, 1993, U.S.A.*

Gaymar Industries, Inc., Medi–Therm II Hyper/Hypothermia Machine MTA5900 Series—Operator's Manual, Nov. 1998, U.S.A.*

The Complete and Autoritative Guide Caring for your Baby and Young Child; Shelov, M.D.; p. 603; copyright 1991, 1993, 1998.*

The Principles and Practice of Medicine; Rustomjee Naserwanjee Khory; pp. 327–329, 1885.*

Sams Temperature Control and Monitor System Operators Manual; Mar. 1985.

Sams TCM II brochure; publication date unknown; copyright 1989.

Gaymar Industries, Inc., Medi–Therm II Hyper/Hypothermia Machine MTA5900 Series—Operator's Manual, Nov. 1998, U.S.A.

Caruso, C.C. et al., Cooling Effects and Comfort of Four Cooling Blanket Temperatures in Humans with Fever, Nursing Research, vol. 41 No. 2, pp. 68–72, Mar./Apr. 1992, U.S.A.

Boggs, R.L. and Wooldridge–King, M., editors, AACN Procedure Manual For Critical Care—3rd Edition, W.B. Saunders Co., p. 443, 1993, U.S.A.

Hubbard, R.W. et al., Rapid Hypothermia Subsequent to Oral Nicotinic Acid Ingestion and Immersion in Warm (30° C) Water, Amer Jrnl of Emerg Med, vol. 6 No. 3, p. 316–17, May 1988, USA.

Gaymar Industries, Inc., MTA6900 MediTherm® III Hypo/Hyperthermia Unit Automatic Modes: Rapid, Moderate, and Gradual Settings, Oct. 2005, U.S.A.

U.S. District Court, Western District of New York, Case No. 1:08–CV–00299–WMS, Transcript of the Deposition of Edward S. Wells taken Sep. 24, 2008 at Ann Arbor, MI.

U.S. District Court, Western District of New York, Case No. 1:08–CV–00299–WMS, Transcript of the Deposition of Thomas P. Stewart taken Oct. 1, 2008 at Buffalo, NY.

U.S. District Court, Western District of New York, Case No. 1:08–CV–00299–WMS, Transcript of the Deposition of Donald F. Woodworth, Jr. taken Oct. 2, 2008 at Buffalo, NY.

U.S. District Court, Western District of New York, Case No. 1:08–CV–00299–WMS, Transcript of the Deposition of Robert Mates taken Oct. 7, 2008 at Buffalo, NY.

U.S. District Court, Western District of New York, Case No. 1:08–CV–00299–WMS, Transcript of the Deposition of Hermann Karl Pohl taken Oct. 8, 2008 at Buffalo, NY.

U.S. District Court, Western District of New York, Case No. 1:08–CV–00299–WMS, Transcript of the Deposition of Steven J. Berke taken Oct. 29, 2008 at Cincinnati, OH.

U.S. District Court, Western District of New York, Case No. 1:08–CV–00299–WMS, Transcript of the Deposition of Richard Allen Killworth taken Nov. 4, 2008 at Dayton, OH.

U.S. District Court, Western District of New York, Case No. 1:08–CV–00299–WMS, Transcript of the Deposition of Danial Koewler taken Nov. 5, 2008 at Cincinnati, OH.

* cited by examiner

INTER PARTES REEXAMINATION CERTIFICATE ISSUED UNDER 35 U.S.C. 316

THE PATENT IS HEREBY AMENDED AS INDICATED BELOW.

AS A RESULT OF REEXAMINATION, IT HAS BEEN DETERMINED THAT:

Claims 1-134 are cancelled.

* * * * *